US006634234B1

United States Patent
Haas

(10) Patent No.: US 6,634,234 B1
(45) Date of Patent: Oct. 21, 2003

(54) ADJUSTABLE MEASUREMENT HEAD AND A LEVEL MEASUREMENT DEVICE AND METHOD EMPLOYING IT

(75) Inventor: Dieter Haas, Lauterbach (DE)

(73) Assignee: Vega Grieshaber KG, Wolfach (DE)

( * ) Notice: Subject to any disclaimer, the term of this patent is extended or adjusted under 35 U.S.C. 154(b) by 0 days.

(21) Appl. No.: 10/058,314

(22) Filed: Jan. 30, 2002

Related U.S. Application Data
(60) Provisional application No. 60/273,329, filed on Mar. 6, 2001.

(30) Foreign Application Priority Data

Feb. 10, 2001 (DE) .......................................... 101 06 176

(51) Int. Cl.[7] ........................ G01N 29/04; G01N 24/00; G01F 23/00; H04B 1/02
(52) U.S. Cl. ........................ 73/618; 73/290 V; 73/620; 73/629; 73/633; 367/138
(58) Field of Search ................. 73/290 V, 291, 73/618, 633, 629, 290 R, 620; 340/619, 621; 367/138, 140, 190; 250/577, 900

(56) References Cited

U.S. PATENT DOCUMENTS

| | | | | |
|---|---|---|---|---|
| 3,842,894 A | * | 10/1974 | Southworth et al. | 164/453 |
| 4,114,441 A | * | 9/1978 | Magri | 73/290 V |
| 4,151,834 A | * | 5/1979 | Sato et al. | 600/446 |
| 4,202,398 A | * | 5/1980 | Osugi | 164/151.3 |
| 4,215,585 A | * | 8/1980 | Kunii et al. | 73/633 |
| 4,247,989 A | * | 2/1981 | Steffen | 34/428 |
| 4,280,126 A | * | 7/1981 | White | 340/621 |
| 4,341,120 A | * | 7/1982 | Anderson | 73/618 |
| 4,637,256 A | * | 1/1987 | Sugiyama et al. | 73/633 |
| 5,337,289 A | * | 8/1994 | Fasching et al. | 367/140 |
| 6,098,029 A | | 8/2000 | Takagi et al. | 702/127 |

FOREIGN PATENT DOCUMENTS

| | | |
|---|---|---|
| DE | 3113248 | 3/1987 |
| DE | 19504579 | 8/1996 |

* cited by examiner

Primary Examiner—Helen Kwok
Assistant Examiner—Katina Wilson
(74) Attorney, Agent, or Firm—Nath & Associates PLLC; Gary M. Nath; Marvin C. Berkowitz

(57) ABSTRACT

A measurement head for a device for measuring the level of a product in a container comprises a transmitter/receiver unit to transmit a scanning signal and receive an echo of the scanning signal returned by the product, a fastening element to fasten the transmitter/receiver unit to a support and at least one actuator to move the transmitter/receiver unit relative to the fastening element.

16 Claims, 5 Drawing Sheets

ADJUSTABLE MEASUREMENT HEAD AND A LEVEL MEASUREMENT DEVICE AND METHOD EMPLOYING IT

This application is a non-provisional of U.S. provisional application No. 60/273,329 filed Mar. 6, 2001.

FIELD OF THE INVENTION

The present invention concerns a level measurement device with an adjustable measurement head and such a measurement head, as well as a level measurement method.

BACKGROUND OF THE INVENTION

Level measurement devices, like, radar and ultrasonic sensors or optical systems, are used to determine the level of a product in a container or in the open. The shapes of the containers can vary sharply. In order to be able to use a measurement head in conjunction with various container geometries, it is known to provide them with a swivel mount that can be mounted at an appropriately selected location on the container wall, making it possible to establish the alignment of the transmitter/receiver unit of the measurement head, so that a satisfactory, reliably evaluable echo signal is obtained, if possible, under all operating conditions.

This type of measurement head has various drawbacks. In the first place, the quality of the measurements that can be obtained with such a measurement head depend strongly on how skillfully or unskillfully the incorporation position and alignment of the measurement head on the container were chosen. An improperly selected incorporation position can mean that useful measurements are only possible at certain filling levels. Generally, this means that extremely low levels or regions with interfering echoes are excluded from the useful measurement interval. However, it is precisely the extreme level values whose recording is particularly important, in order to avoid overfilling or emptying of the container. One can objectively assume that, in a bulk product container, a central, downward oriented mounting of the measurement head should be optimal, in order for the scanning signal emitted by the measurement head to always encounter the filling level and not be scattered on the container walls. This type of mounting, however, means that the measurement head lies directly opposite the tip of a product cone, which forms during filling of the container via a filling connector arranged in the center for technical reasons, so that, with a high filling level, the distance between the product and measurement head falls short of a minimum distance necessary for correct processing of the reflected echo signal. In addition, this type of scanning signal is very strongly influenced by the product stream during filling of the container, so that, precisely in this critical phase, a reliable measurement is not possible. An off-center, downward oriented mounting of the measurement head means that the beam of the scanning signal, propagating cone-like from the measurement head, is scattered more strongly on the container wall, the lower the level, so that low levels are not satisfactorily recorded here. An orientation of the measurement head deviating from the vertical means that, at low levels, the axis of the scanning signal cone can intersect the container wall, which is also undesirable.

SUMMARY OF THE INVENTION

The objective of the present invention is to provide a measurement head for a device for measuring the level of a product and such a device, which avoids the aforementioned alignment problems, and which is therefore easily installable by untrained personnel and suitable for obtaining more reliable measurement results.

The objective is realized, in the first place, by a measurement head with the features of claim 1 and, in the second place, by a level measurement device with the features of claim 4.

The measurement head according to the invention is equipped with at least one actuator to move the transmitter/receiver unit relative to its fastening element. This type of actuator can also always be operated after installation of the measurement head, if an unsatisfactory echo signal is received in a given position of the measurement head.

This type of actuator can be used to rotate or shift and/or tilt the measurement head; naturally, several actuators can also be combined, in order to move the measurement head in several degrees of freedom of rotation and/or translation.

The level measurement device according to the invention is equipped with such a measurement head and a control unit to operate its at least one actuator.

Automatic control of excitation of the actuator can occur according to various criteria. A first basic principle of control of the actuator is evaluation of the quality of the echo signal received in a given position by the control unit and operation of the actuator to vary the position of the measurement head when this quality is evaluated as deficient. Various criteria are conceivable for evaluation of the quality; for example, a signal can be considered deficient if its intensity or the signal/noise ratio falls short of a limiting value, or if the travel time of the echo signal lies outside of an admissible interval. The lower limit of this interval is generally defined by the aforementioned minimum spacing required for correct processing of the echo signal; the upper limit can be defined differently for different measurement positions. More precisely, the definition corresponds to the upper limit of travel time of an echo signal and the corresponding position of the measurement head with an empty container. This upper limit can be stipulated from the outside, for example, calculated beforehand as a function of the container geometry and entered in the control unit, but it is much more convenient and more flexible if the control unit defines the admissible interval for a position of the measurement head by means of a measurement conducted on the container in the empty state with the same position of the measurement head. This means it is assumed that the signal travel time in a non-empty container in each case must be shorter than the time measured in an empty container, so that the travel time measured in the empty container can be established as the upper limit of the interval.

The adjustability of the measurement head can also be used to perform measurements in different positions of the measurement head that correspond to different impingement regions of the signal cone on the product level. The variety of measured values so obtained can be used to record the surface profile of the product in the container and to calculate a quantity based on it for the volume of the product. In order to calculate the amount of product beneath the recorded level for such a calculation, a control unit requires stored data concerning the shape of the container. These data can be entered in the control unit beforehand, but the possibility of having the control unit generate these data itself by measurements conducted on the container in the empty state is particularly convenient and flexible.

It is also expedient if the control unit compares the measured values obtained for a variety of measurement head positions with an expected surface profile and discards the measured values whose deviation from the expected surface profile exceeds a limit value. This expected surface profile can have the shape of a debris cone or the like with a surface trend characteristic of the product being monitored. The level of this debris cone or the like in the container can be adjusted by means of the variety of obtained measured values, for example, by an optimization method, for example, according to the criterion of mean square error. If a measurement value is obtained in one position that deviates excessively from the value adapted to the expected debris cone or the like, it can be assumed that the measurement is disturbed in this position and the measurement value can be rejected. The deviation of the measured value obtained in an individual position from an expected surface-profile can also be used as a criterion for the quality of the echo signal at this position and cause the control unit to adjust a different position of the measurement head for continued measurement.

Moreover, the control unit can be designed so that excess deviations from the expected container profile recorded with time are used by the measurement head to generate warning messages. An operating person can therefore be simply informed about unusual changes within the measurement space.

Additional features and advantages of the invention are apparent from the following description of embodiment examples with reference to the figures. In the figures:

DETAILED DESCRIPTION

Figure 1:
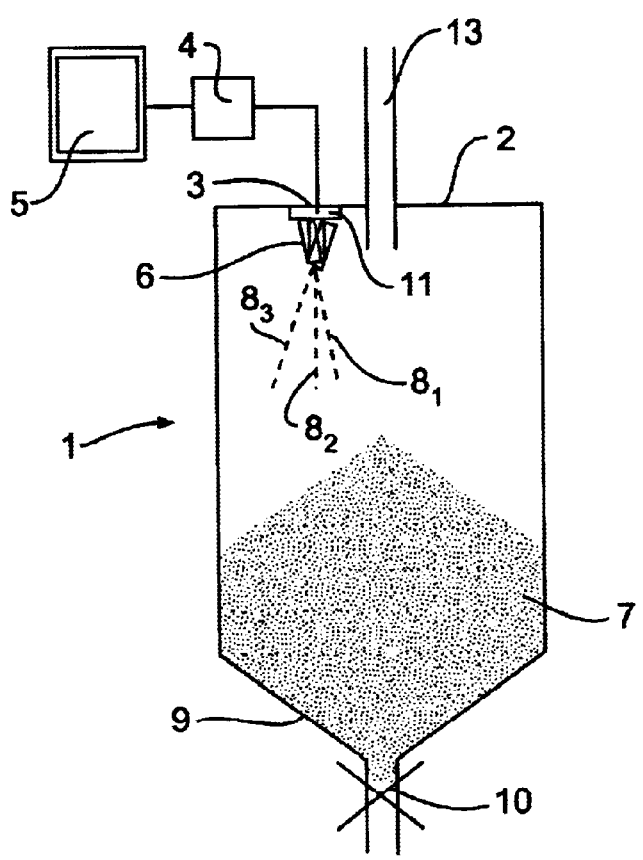
FIG. 1 shows a schematic section through a bulk product container equipped with a level measurement device according to the invention.

FIG. 1 shows, in a schematic vertical section, a container with a level measurement device. The level measurement device includes a measurement head 3 mounted in the interior of container 1 on its cover 2, a control unit 4 connected to measurement head 3, as well as a display unit 5, for example, a display. The control unit 4 can be implemented as an appropriately programmed microprocessor connected to measurement head 3; however, it can also be an unspecialized computer that communicates with the measurement head 3 via an interface (not shown) and is capable of processing a program whose process steps are explained more precisely below.

The measurement head 3 comprises a transmitter/receiver unit 6 to transmit a scanning signal, especially a radar or ultrasound signal (optical signals are also possible) into the lower region of container 1, where a product 7 being recorded is situated, and to receive an echo signal returned by the product 7; a fastening element to fasten the transmitter/receiver unit 6 to the cover 2 of container 1, functioning as support; and an actuator 11, operable by control unit 4, in order to vary the orientation of the transmitter/receiver unit 6. An arbitrary servo-element that is capable of varying the orientation of the transmitter/receiver unit 6 with reference to container 1 and keeping it in an adjusted orientation is suitable as actuator 11. The measurement head 3 is shown in FIG. 1 in three different orientations, to which the axes of the scanning beam, denoted 81, 82, 83, correspond.

With the approximately center level of the product 7 shown in the figure, the scanning beams $8_1$, $8_2$ encounter the product level and there generate an echo, recordable by the transmitter/receiver unit 6. The scanning beam $8_3$, on the other hand, initially impinges on the container wall and is reflected from it before it reaches the product 7. It is therefore assumed that the scanning beams $8_1$, $8_2$ will furnish a useful echo signal; beam $8_3$, on the other hand, will not.

At a high level, the product 7 can come very close to measurement head 3, so that reliable recording of a useful echo is no longer possible: Since the beam $8_3$ does not intersect the container wall with this high level before it encounters the product 7, the orientation corresponding to beam $8_3$ is suitable in this situation.

At a low level, a problem can arise for scanning beam $8_2$ in that it impinges on the conical bottom 9 of the container 1 before the container is actually empty, and that the remaining amount of product still present in this state can no longer be recorded. If the scanning beam deviates strongly from the measurement head 3, an additional problem arises in that the fraction of the scanning beam reflected on the container walls before it encounters the product becomes increasingly larger with diminishing levels, so that the measurement reliability and accuracy diminish gradually with a dropping level. The beam $8_1$ oriented in the direction of the container outlet 10 is therefore better suited for level measurement at low levels. It is easy to see that this problem is easy to eliminate by means of the actuator 11, which is operated by control unit 4, in order to adjust he position of measurement head 3 in the case of measurement problems or to cyclically search for better measurement positions.

Figure 2A:
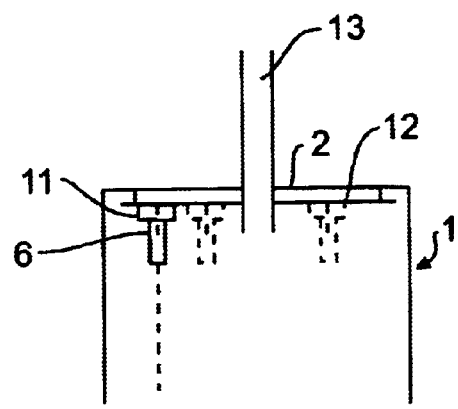
FIG. 2a shows a section through the upper region of a bulk product container according to a second embodiment.
Figure 2B:
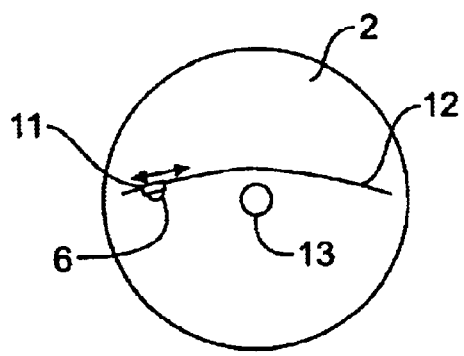
FIG. 2b shows a horizontal section through the upper region of the bulk product container.

Before going into the manner of this adjustment, alternative possibilities for mounting the measurement head must still be briefly mentioned. Whereas the fastening element in the measurement head of FIG. 1 has the shape of a simple arm, on which the transmitter/receiver unit 6 is pivotable, in the embodiment example of FIGS. 2a, 2b, the fastening element is designed instead as a rail 12 that runs along the cover 2 of container 1. As the horizontal section of FIG. 2b shows, the rail 12 runs between two diametrically opposite sides of container 1 slightly curved, in Ad A order to bypass the filling connector 13 mounted in the center of cover 2. A linear drive element for displacement of the transmitter/receiver unit 6 along rail 12 serves as actuator 11 in this case. An additional actuator (not shown) can be provided to pivot the transmitter/receiver unit 6 with reference to rail 12 with one or two degrees of rotational freedom.

Figure 3:
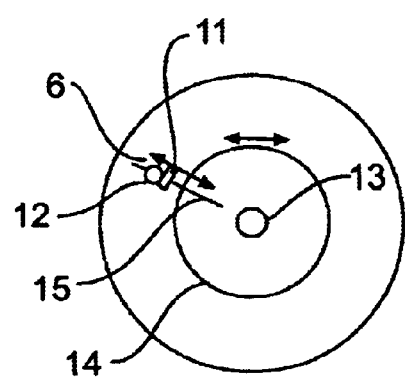
FIG. 3 shows a horizontal section through the upper region of a bulk product container according to a third embodiment of the invention.

Another embodiment with a fastening element designed as a rail system is shown in FIG. 3. The rail system consists of a first rail 14 extending in a circle around the vertical axis of the container 1 or filling connector 13 and a radially oriented second rail 15 movable on it, on which the transmitter/receiver unit 6 is mounted to travel. By means of this rail system, the transmitter/receiver unit 6 can be positioned at virtually any point on the cover 2 of container 1.

The transmitter/receiver unit 6 can be designed so that it generates sharply bundled scanning beams. Since the transmitter/receiver unit 6 can assume a number of positions in each of the aforementioned embodiments, it is not essential that an evaluable echo signal be received in each individual position. Whereas in the case of a nonmoving transmitter/receiver unit, a significant beam opening angle is required in order to guarantee that the beam always encounters a section of the surface of the product that can yield a useful echo, a transmitter/receiver unit 6 can and should preferably be used, in the context of the present invention, whose scanning beam, even at a low level, scans no more than 25%, preferably much less than 10%, of the surface of the product 7. The number of foreign objects that do not belong to the product surface being recorded and are encountered by the scanning beam and produce interferences in the echo signal is naturally smaller, the more strongly bundled the beam. Evaluation of the echo signal is also simplified accordingly with sharper-bundling.

Figure 4A:
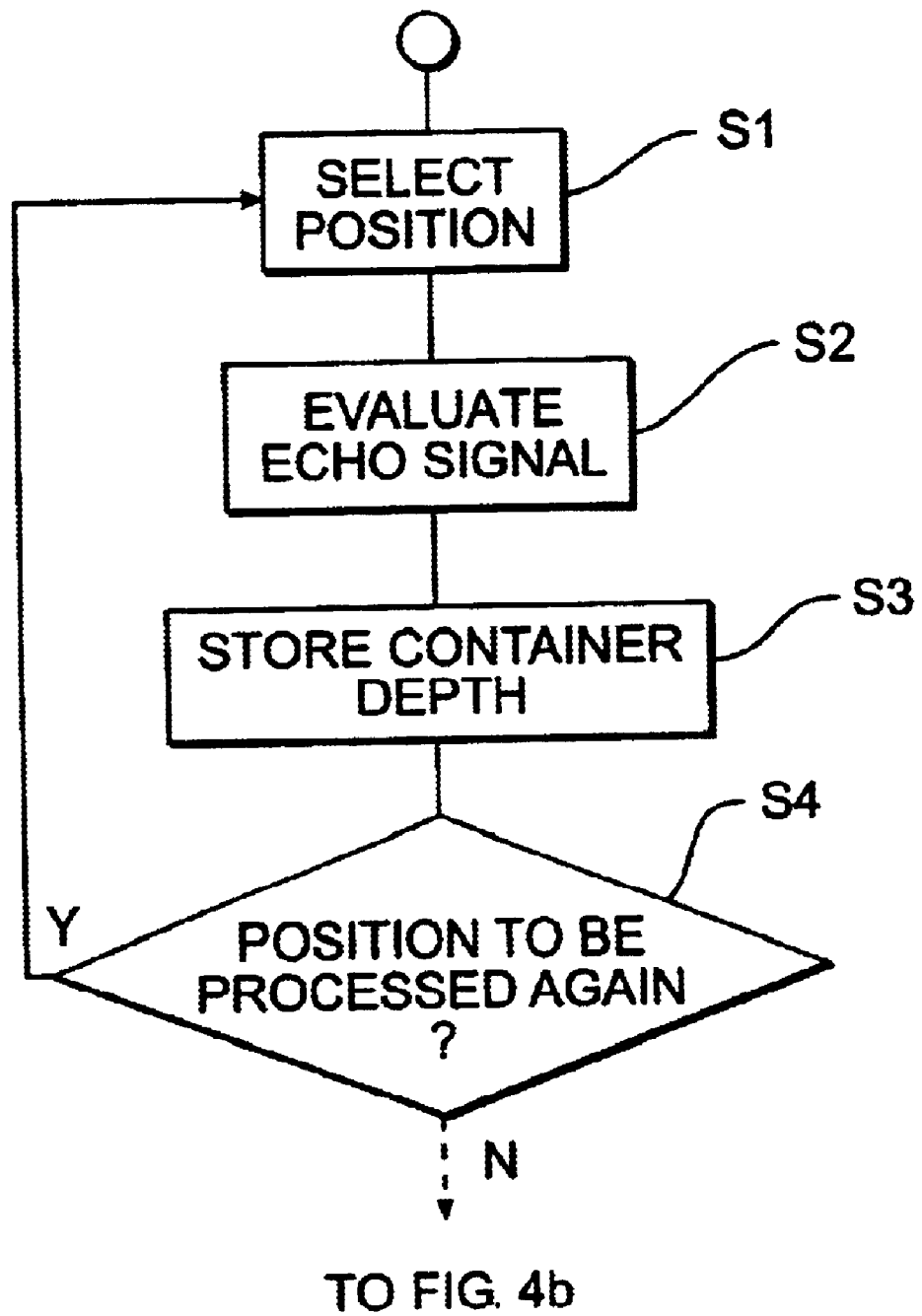
FIG. 4a shows an initialization method, conducted by the level measurement device according to the invention.

A first example for the method of operation of control unit 4 will now be described with reference to FIGS. 4a and b. FIG. 4a concerns an initialization that is carried out each time the level measurement device is newly installed or design changes have been made on container 1.

By means of the actuator 11 (or optionally several actuators) a variety of positions of the transmitter/receiver unit 6 are adjustable. One such position is chosen in step S1, the scanning signal is emitted and the received echo signal is evaluated in step S2. If the container 1 is empty, the container height at the adjusted position can be estimated by means of the travel time of the received echo signal. The obtained value is stored in step S3. This sequence of steps is repeated until it has been performed for the variety of positions of the transmitter/receiver unit 6.

Figure 4B:
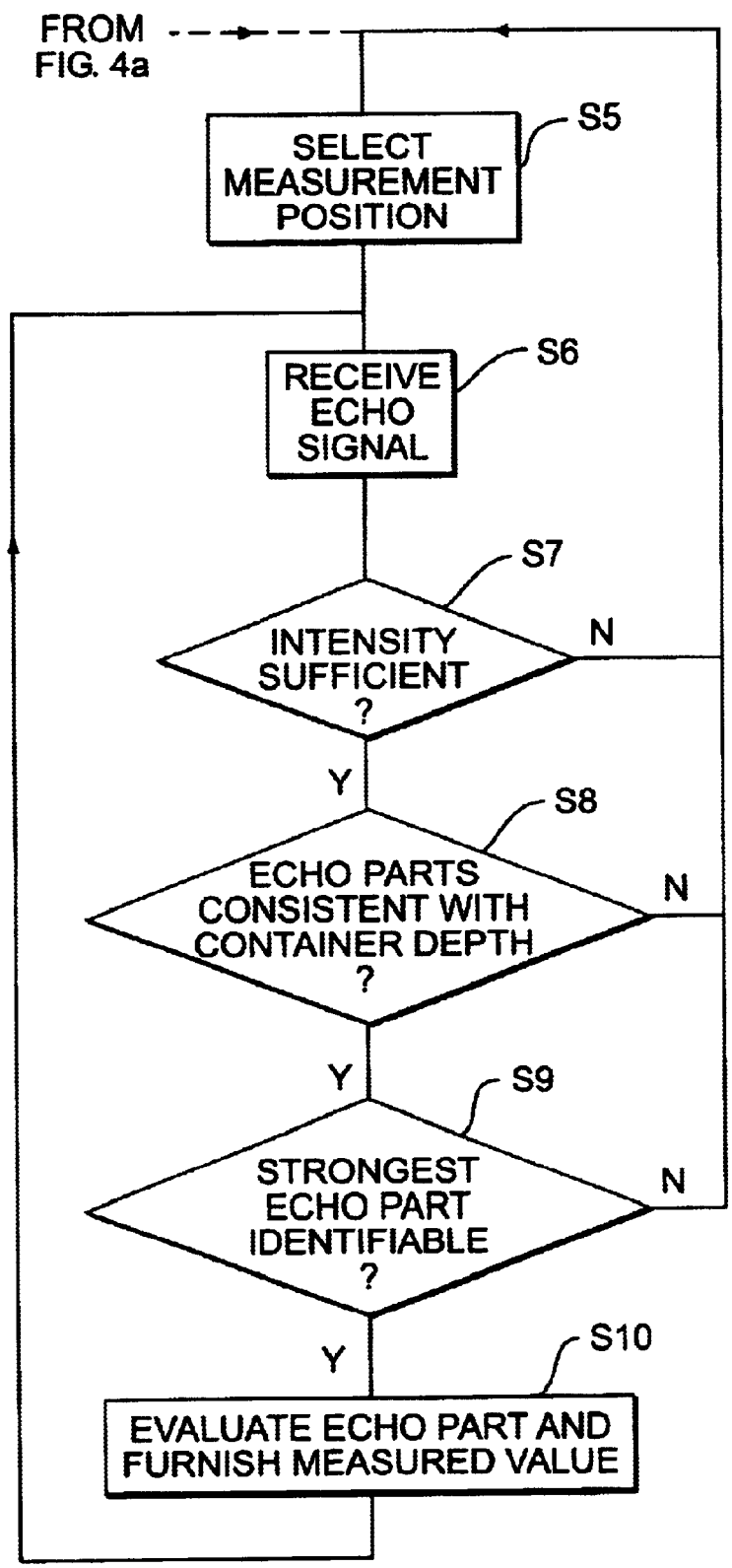
FIG. 4b shows a first embodiment of an operating method of the level measurement device.

FIG. 4b shows the process steps conducted during continuous level monitoring. Initially, in step S5, one of the different possible measurement positions is chosen. An echo-signal is received in step S6 and it is evaluated whether its quality is sufficient to permit sufficiently reliable level measurement. For this purpose, the intensity of the echo signal is initially compared in step S7 with a stipulated limit value. If the echo signal is too weak, this is a strong indication that it is not due to a direct reflection of the scanning signal on the surface of the product, and that therefore its evaluation cannot lead to a correct measurement result (note: with weak echo signals or a completely different echo pattern, filling can also be present. A weak echo can therefore also be a useful echo.).

If the intensity of the measurement signal is-found to be sufficient, the process proceeds further to step S8, in which the travel times of the most important parts of the echo signal are compared with the container depth, measured during initialization for the corresponding measurement position. Parts whose travel time suggests greater distance of the echo source from the transmitter/receiver unit 6 than that corresponding to the container depth can be attributed to multiple reflection and are therefore unusable. If the echo signal also contains parts with sufficiently shorter travel time, the process proceeds to step S9, in which it is checked whether the strongest part is identifiable among the parts with shorter travel time. If so, the echo signal can be evaluated in step S10 and a measured value delivered.

Otherwise, i.e., if, among several parts with shorter travel time none is present that is significantly stronger than the others, the measured signal is evaluated as deficient. In this case, the actual measurement position is obviously unsuitable for a measurement and the method returns to step S5, where a new measurement position is chosen.

Generally, it can be stated that, if the echo signal exhibits features, for example, a signal/noise ratio, amplitude or the like, that prevent a distinct evaluation or suggest it is uncertain, a new measurement position can always be chosen.

Figure 5:
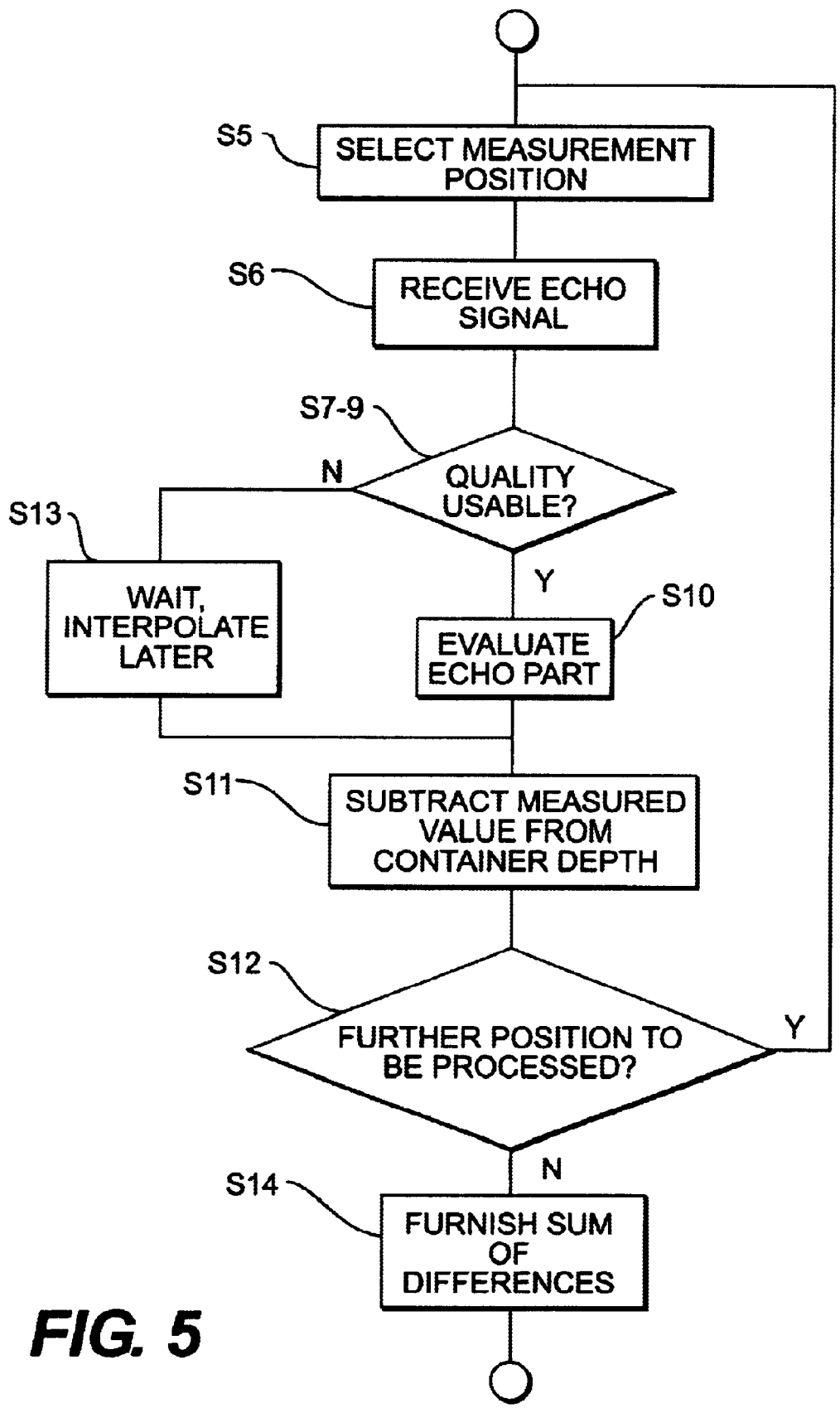
FIG. 5 shows a second embodiment of an operating method.

The measurement head according to the invention naturally can be used not only to generate an individual level measurement value, but this type of measurement head can also be used to reliably "chart" its surface by level measurements at different sites of the surface of the product, simultaneously or in close succession. FIG. 5 shows this type of method. It is also based on initialization conducted beforehand for the different measurement positions according to FIG. 4a. As in the case of FIG. 4b, one measurement position is initially chosen and an echo signal received in this position. Evaluation of the quality, denoted S7–9 in FIG. 5, can occur in the same manner as described in FIG. 4b. If the measurement signal is evaluated as useful, it is evaluated in step S10, and the calculated level is subtracted in step S11 from the container depth, determined beforehand for the corresponding measurement position. Steps S5 to S11 are repeated over all measurement positions, so that finally a number of different values are available that indicate, for each measurement point, the height of the product column above the bottom. With reference to a number of such values, the corresponding values can be obtained by interpolation for adjacent positions for those positions at which no useful echo signal was received (step S13). By appropriate summation or integration over the obtained different values, the volume of the product in the container is finally obtained (step S14).

Figure 6:
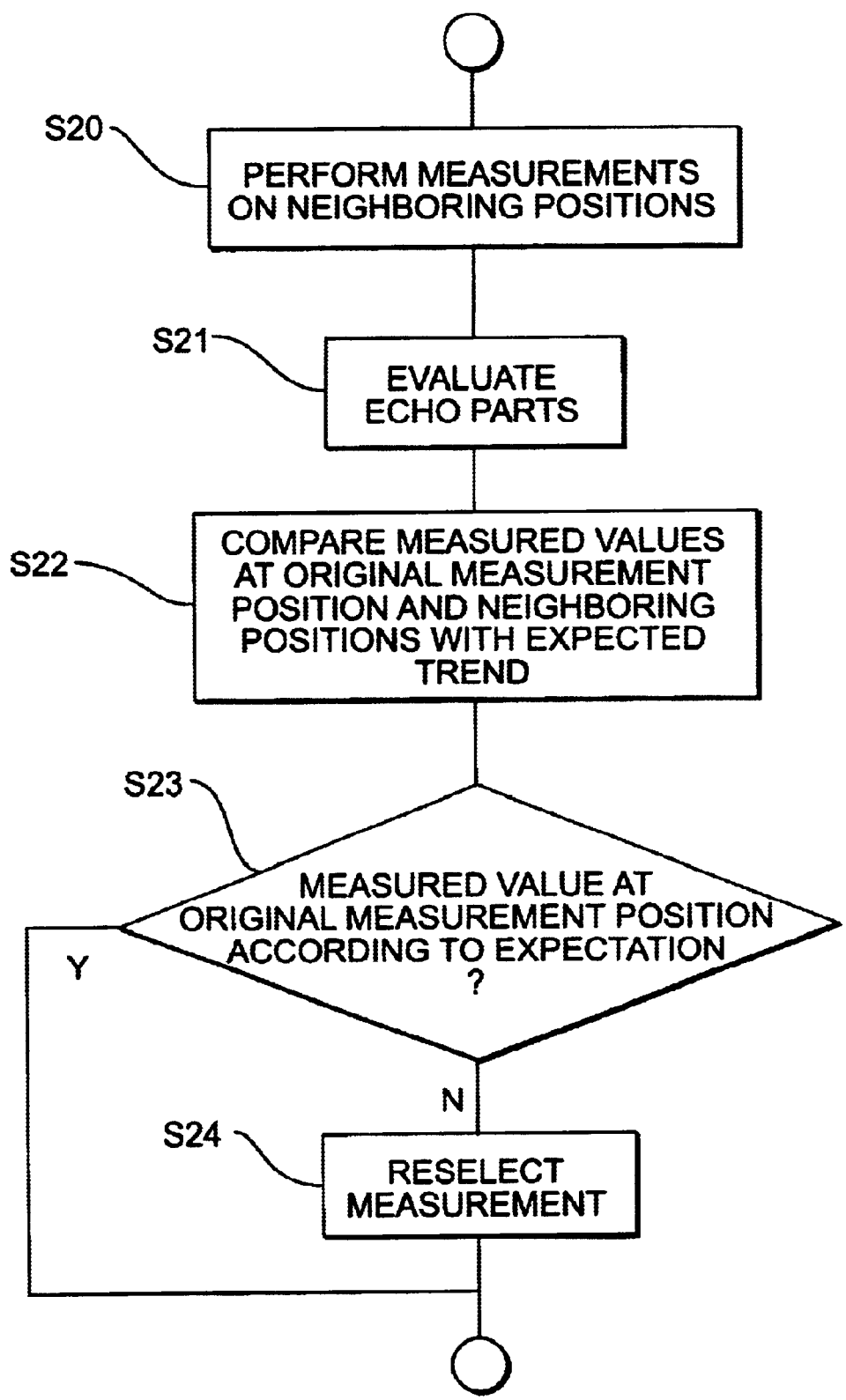
FIG. 6 shows process steps of a modified variant of the operating method of FIG. 4b.

Measurements on positions adjacent to an adjusted measurement position can also be used to evaluate the quality of an echo signal at the adjusted measurement position. FIG. 6 shows process steps that can be inserted for this purpose at any site between steps S6 to S10 of the process according to FIG. 4b. In a first of these steps S20, measurements are made on a variety of neighboring positions of the adjusted measurement position. With reference to the received echo signals, level values are determined in step S21 for the different neighboring positions. These measured values and the value obtained at the adjusted measurement position are compared with an expected trend of the surface of the product (S22). A debris cone, with the angle of slope characteristic of the corresponding product, can be assumed as expected trend, whose center level can also be estimated from all of the measured values at the adjusted measurement position and the neighboring positions. It is also conceivable to assume, as expected trend, an average value of surface trends measured previously for the same average filling level. If the measured value at the adjusted measurement position, in the context of an assumed measurement accuracy of the level measurement device, coincides with the expected trend (23), the adjusted measurement position is then considered suitable and measurement operations can be continued at the adjusted position. If the measured value at the adjusted measurement position deviates excessively from the expected trend, this suggests a measurement error that can be attributed to irregularities in the surface structure of the product or to the fact that the scanning beam encounters a product that remained adherent to the wall of container 1 during emptying, whereas the surface of the main mass of the product receded farther. In this case, a measurement position is again chosen in a step S24. One of the neighboring positions that yielded a good measured value corresponding to the expectation can be used as the new measurement position.

What is claimed is:

1. Measurement head for a device for measurement of the level of a product, with a transmitter/receiver unit to emit a scanning signal and receive an echo of the scanning signal returned by the product and a fastening element to fasten the transmitter/receiver unit to a support, characterized by:

at least one actuator to move the transmitter/receiver unit relative to the fastening element;

a control unit to operate said at least one actuator; wherein said control unit is set up to evaluate a quality of the echo signal received in a stipulated position and to operate the actuator to vary the position, if the quality is evaluated as deficient.

2. Measurement head according to claim 1, characterized by the fact that the transmitter/receiver unit is rotatable by said at least one actuator.

3. Measurement head according to claim 1, characterized by the fact that the transmitter/receiver unit is movable and/or tiltable by said at least one actuator.

4. Level measurement device according to claim 1, characterized by the fact that the control unit evaluates the quality of the echo signal as deficient, if its intensity and/or signal/noise ratio falls below a limit value.

5. Level measurement device according to claim 1, characterized by the fact that the control unit evaluates the quality of the echo signal as deficient, if a travel time of the echo signal lies outside of an admissible interval.

6. Level measurement device according to claim 5, characterized by the fact that the admissible interval is defined differently for different measurement positions.

7. Level measurement device according to claim 6, characterized by the fact that the control unit defines the admissible interval for a position by means of a measurement conducted on a container in an empty state.

8. Level measurement device according to claim 1, characterized by the fact that the control unit evaluates the quality of the echo signal as deficient if it has several similarly strong parts with different travel times.

9. Level measurement device according to claim 1, characterized by the fact that the control unit calculates a quantity representative of a volume of the product by means of measurements conducted in different positions of the measurement head.

10. Level measurement device according to claim 9, characterized by the fact that the control unit performs the calculation by means of stored data concerning a shape of a container.

11. Level measurement device according to claim 10, characterized by the fact that the control unit generates the data concerning the shape of the container by means of measurements conducted on the container in an empty state.

12. Level measurement device according to claim 1, characterized by the fact that the control unit generates a surface profile of the product level by means of measured values obtained in different positions of the measurement head.

13. Level measurement device according to claim 1, characterized by the fact that the control unit evaluates as deficient the quality of the echo signal, whose deviation from an expected surface profile exceeds a limit value.

14. Method for measurement of a level by means of a measurement head with the steps:

a) transmitting of a scanning signal and receiving of a returned echo, b) evaluation of a quality of the returned echo, c) if the quality is evaluated as deficient, variation of a position of the measurement head and repetition of steps a) to c); otherwise d) evaluation of the echo and furnishing of a measured value.

15. Method according to claim 14, characterized by the fact that the measured value being furnished is calculated from echo signals obtained for several different positions of the measurement head.

16. Method according to claim 15, characterized by the fact that a volume of a product is calculated as the measured value.

* * * * *